United States Patent [19]

Kim et al.

[11] Patent Number: 4,565,815

[45] Date of Patent: Jan. 21, 1986

[54] PYRAZOLO[1,5-A]-1,3,5-TRIAZINES

[75] Inventors: Sun H. Kim, Chestnut Hill; Jacques-Pierre Moreau, Upton, both of Mass.

[73] Assignee: Biomeasure, Inc., Hopkinton, Mass.

[21] Appl. No.: 614,454

[22] Filed: May 25, 1984

Related U.S. Application Data

[63] Continuation-in-part of Ser. No. 454,734, Dec. 30, 1982, abandoned.

[51] Int. Cl.[4] .................. C07D 487/04; C07D 403/14; C07D 407/14; A61K 31/415
[52] U.S. Cl. ..................... 514/246; 544/211; 544/212; 544/113; 544/206; 544/245; 544/197; 544/198; 544/207; 544/219; 544/216; 544/180
[58] Field of Search ............ 544/207, 209, 211, 212, 544/219, 113, 216, 180, 206; 514/245, 246

[56] References Cited

U.S. PATENT DOCUMENTS 4,128,658 12/1978 Price et al. .................. 424/285

FOREIGN PATENT DOCUMENTS 875846 10/1979 Belgium .
1397436 6/1975 United Kingdom .

OTHER PUBLICATIONS

Lumma et al. (1982) J. Med. Chem., 25 207–210.
Algieri et al. (1982) J. Med. Chem. 25 210–212.

Primary Examiner—John M. Ford

[57] ABSTRACT

A compound having anti-ulcer activity and having the formula

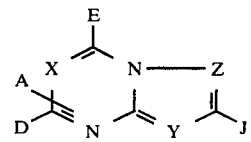

wherein D is H, SH, $NH_2$, OH, $R^4S$ where $R^4$ is a lower alkyl group; E is OH or $NH_2$; J is H or aryl; X is CH or N; Y is CH, N, or CT, wherein T is a halogen; Z is CH or N; A is

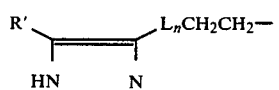

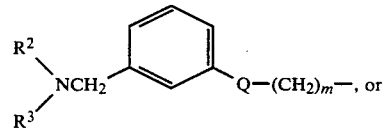

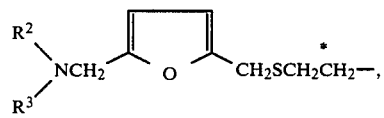

and replaces a hydrogen of D, X, or E; $R^1$ is H or $CH_3$; L is $CH_2S$; Q is O or $CH_2S$; n is 0 or 1; 2 m 4; each $R^2$ and $R^3$, independently, is H, lower alkyl, cycloalkyl, or arylalkyl; or $R^2$ and $R^3$, together with the nitrogen atom to which they are attached, form a 4, 5, or 6 membered heterocyclic ring containing 0, 1, or 2 oxygen atoms and 1, 2, or 3 nitrogen atoms and being unsubstituted or lower alkyl substituted; or a pharmaceutically acceptable salt thereof.

14 Claims, No Drawings

PYRAZOLO[1,5-A]-1,3,5-TRIAZINES

BACKGROUND OF THE INVENTION

This application is a continuation-in-part of Kim et al. U.S. patent application Ser. No. 454,734, filed Dec. 30, 1982, now abandoned.

This invention relates to compounds that prevent formation of gastric or duodenal ulcers, either by inhibition of gastric acid secretion, or by other mechanisms.

Such compounds may prevent ulcers caused by a variety of stimuli, e.g., histamine, gastrin, food, parasympathetic activity, and the non-steroidal anti-inflammatory drugs.

SUMMARY OF THE INVENTION

In general, the invention features compounds having anti-ulcer activity and having the general formula

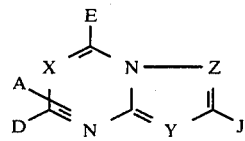

(1)

wherein D is H, SH, OH, $NH_2$, or $R^4S$ where $R^4$ is lower (fewer than 7 carbon atoms) alkyl; E is OH or $NH_2$; J is H or an aryl group (having, preferably, a single ring); X is CH or N; Y is N, CH, or CT, wherein T is a halogen; Z is CH or N; and A replaces a hydrogen of X, D, or E and is chosen from

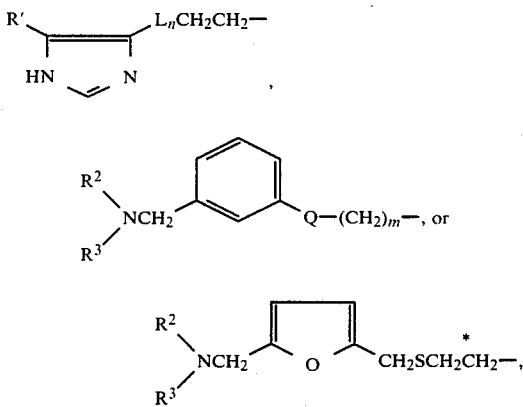

wherein $R^1$ is H or $CH_3$; L is $CH_2S$; Q is O or $CH_2S$; n is 0 or 1; 2 m 4; each $R^2$ and $R^3$, independently, is hydrogen, lower alkyl, cycloalkyl (3 to 6 carbon atoms), or arylalkyl (e.g., benzyl or phenethyl); or $R^2$ and $R^3$, together with the nitrogen atom to which they are attached, form a 4, 5, or 6 membered heterocyclic ring containing 0, 1, or 2 oxygen atoms and 1, 2, or 3 nitrogen atoms and being unsubstituted or lower alkyl substituted (e.g., morpholino, piperidino, or N-alkyl piperazino).

In preferred embodiments X is N; Z is N; J is H or phenyl; Y is CH or CT; and each $R^2$ and $R^3$, independently, is H or a lower alkyl. Specific compounds include 2-(4-imidazolylethylamino)-4-oxo-1H,3H-pyrazolo[1,5-a]-1,3,5-triazine; 4-(2-(5-methyl-4-imidazolylmethylthio)-ethylamino)-2-methylthiopyrazolo[1,5-a]-1,3,5-triazine; 4-(4-imidazolylethylamino)-2-methylthiopyrazolo[1,5-a]-1,3,5-triazine; 8-bromo-4-(2-(5-methyl-4-imidazolylmethylthio)-ethylamino)-2-methylthiopyrazolo[1,5-a]-1,3,5-triazine; 8-bromo-4-(4-imidazolylethylamino)-2-methylthiopyrazolo-[1,5-a]-1,3,5-triazine; 4-[4-imidazolylethylamino]-2-methylthio-7-phenylpyrazolo[1,5-a]-1,3,5-triazine; 4-2[-[[[5-(dimethylamino)methyl-2-furanyl]methyl]thio]ethylamino-2-methylthio-7-phenyl-pyrazolo[1,5-a]-1,3,5-triazine; 4-[2-(5methyl-4-imidazolylmethylthio)-ethylamino]-4-oxo-1H,3H-pyrazolo[1,5-a]-1,3,5-triazine; and 4-2[-[[[5-(dimethylamino)methyl-2-furanyl]methyl]thio]ethylamino-2-methylthio-pyrazolo[1-5-a]-1,3,5-triazine.

In addition to inhibiting gastric secretion, the compounds are useful for inhibiting ulcers induced by non-steroidal anti-inflammatory drugs, and can in themselves act as anti-inflammatory drugs. They can also be used to treat mental depression. 4-2[-[[[5-(dimethylamino)methyl-2-furanyl]methyl]thio]ethylamino-2-methylthio-7-phenylpyrazolo[1,5-a]-1,3,5-triazine is particularly effective in both of these applications.

When injected or administered in the form of a pill, tablet, capsule, or liquid, the compounds are potent, non-mutagenic, stable, and will pass through the stomach without losing their effectiveness.

Other features and advantages of the invention will be apparent from the following description of the preferred embodiments, and from the claims.

DESCRIPTION OF THE PREFERRED EMBODIMENTS

Structure

The compounds of the invention have the general formula (1). Examples of preferred compounds are those referred to as preferred embodiments above.

The compounds are purine base derivatives having a nitrogen at the ring junction. All the compounds can exhibit tautomerism, and the formulas are intended to cover all tautomers.

The compounds or pharmaceutically acceptable salts thereof can be administered alone or in combination with a pharmaceutically acceptable carrier or diluent.

Acceptable salts include hydrochlorides, hydrobromides, and sulfates. Particularly useful organic acid salts are citrates, acetates, maleates, and fumarates.

For oral administration the pharmaceutical composition can most conveniently be in the form of capsules or tablets, which may be slow release tablets. The composition can also be in the form of a dragee or syrup.

Synthesis

The above compounds can be synthesized as follows. A primary amine of Formula (5), (6), or (7)

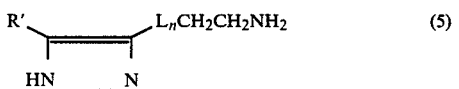

(5)

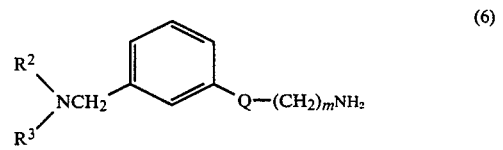

(6)

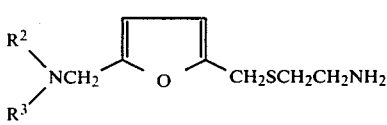

undergoes a condensation reaction with a reagent such as

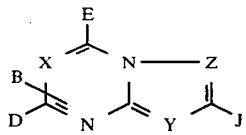

wherein B replaces either D or E and is a good leaving group, e.g., a halogen (e.g. Cl, Br), alkylthio, alkylsulfoxo, or alkylsulfono group. D, E, J, X, Y, and Z in formula (8) are as defined above for Formula (1).

The above reaction will occur either in a protic (e.g., water, alcohol, ethoxyethanol, or ethoxyethoxyethanol) or aprotic (e.g., toluene or xylene) solvent at temperatures from ambient to reflux. The amine can be in the form of the free base or in the form of a salt with a mineral acid, e.g., hydrochloric acid, hydrobromic acid, or sulfuric acid. The primary amines and compounds of Formula 8 are commercially available or easily prepared as described in the literature, e.g., Capuano et al. (1971), Chem. Ber. 104, 3039; Robins et al. (1974), J. Het. Chem 11, 199; Bel Pat. No. 857,388 (1978); Bel. Pat. No. 875,846 (1979); Bel Pat. No. 885,089 (1981).

Specific compounds are made as follows.

2-(4-imidazolylethylamino)-4-oxo-1H,3H-pyrazolo(1,5-a)-1,3,5-triazine

A mixture of 135 mg of free histamine and 180 mg of 2-methylthio-4-oxo-3H-pyrazolo(1,5-a)-1,3,5-triazine in 10 ml of xylene is refluxed for 22 hrs. After evaporation of the solvent in vacuo, the pale pink residue is triturated with water and alcohol, filtered, washed with ether and dried to yield 120 mg of purified product. TLC (silica gel $CHCl_3/MeOH/triethylamine = 3:1:0-5$) Rf=0.14.

4-(2-(5-methyl-4-imidazolylmethylthio)-ethylamino)-2-methylthiopyrazolo[1,5-a]-1,3,5-triazine 500 mg of 4-oxo-2-thioxo-1,2,3,4-tetrahydro-s-triazolo(2,3-a)-5-triazine is dissolved in 3.4 ml of 1.73N NaOH. The solution is diluted with 12 ml methanol, treated with 0.184 ml methyliodide, and stirred at room temperature for ½ hr. The white sodium salt is collected by filtration, redissolved in water, and acidified with $H_2SO_4$. The precipitate is collected by filtration and dried.

100 mg of the resulting 4-oxo-2-methylthio-1,2,3,4-tetrahydro-s-triazolo(2,3-a)-5-triazine are suspended in 1.5 ml of $POCl_3$. Two drops of N,N-dimethylaniline are added, and the mixture is refluxed for 3½ hrs. The $POCl_3$ is removed in vacuo, and the residue treated with ice and $CHCl_3$. The chloroform layer is washed with water several times and dried. 4-chloro-2-methylthio-1,2,3,4-tetrahydro-s-triazolo(2,3-a)-5-triazine is recovered from the chloroform and chromatographed on silica gel using chloroform as the eluant.

The final product of this synthesis is produced by treating with 77 mg of free histamine a solution of 70 mg 4-chloro-2-methylthio-1,2,3,4-tetrahydro-s-triazolo(2,3-a)-5-triazine in 5 ml methanol. The mixture is stirred at room temperature overnight. The yellow precipitate is collected and recrystallized from methanol. Additional product is retrieved from the filtrate after it is concentrated in vacuo. TLC(Silica gel:$CHCl_3/CH_3OH = 3:1$) Rf=0.43.

8-bromo-4-(2-(5-methyl-4-imidazolylmethylthio)-ethylamino)-2-methylthiopyrazolo[1,5-a]-1,3,5-triazine 8-bromo-4-(2-(5-methyl-4-imidazolylmethylthio)-ethylamino)-2-methylthiopyrazolo[1,5-a]-1,3,5-triazine is prepared by brominating 4-(2-(5-methyl-4-imidazolylmethylthio)-ethylamino)-2-methylthiopyrazolo[1,5-a]-1,3,5-triazine, according to conventional methods.

4-(4-Imidazolylethylamino)-2-methylthiopyrazolo(1,5-a)-1,3,5-Triazine

A solution of 30 mg 4-chloro-2-methylthiopyrazolo(1,5-a)-1,3,5-triazine and 33 mg free histamine in 3 ml of methanol is stirred at room temperature overnight. After evaporation of solvent, the residue is dissolved in ethylacetate, washed with water, and dried over $MgSO_4$. After removal of solvent, the residue is subject to silica gel preparative thin layer chromatography using $CHCl_3$/methanol=9:1 as a developing solvent. Appropriate fractions are isolated, extracted with $CHCl_3/CH_3OH$ (3:1), and solvent removed in vacuo to dryness. 20 mg of a white solid are recovered. TLC (silica gel $CHCl_3/CH_3OH=3:1$) Rf=0.15.

8-bromo-4-(4-imidazolylethylamino)-2-methylthiopyrazolo-[1,5-a]-1,3,5-triazine 8-bromo-4-(4-imidazolylethylamino)-2-methylthiopyrazolo-[1,5-a]-1,3,5-triazine is prepared by brominating 4-(4-imidazolylethylamino)-2-methylthipyrazolo(1,5-a)-1,3,5-triazine according to conventional methods.

4-[4-imidazolylethylamino]-2-methylthio-7-phenylpyrazolo[1,5-a]-1,3,5-triazine

4-[4-imidazolylethylamino]-2-methylthio-7-phenylpyrazolo[1,5-a]-1,3,5-triazine is prepared from histamine and 4-chloro-2-methylthio-7-phenylpyrazolo[1,5-a]-1,3,5-triazine according to conventional methods.

4-2[-[[[5-(dimethylamino)methyl-2-furanyl]methyl]thio]ethylamino-2-methylthio-7-phenylpyrazolo[1,5-a]-1,3,5-triazine 4.82 g 4-methoxy-2-methylthio-7-phenylpyrazolo[1,5-a]-1,3,5-triazine is suspended in 100 ml of methanol and a solution of 4.3 g 2-[[[5-(dimethylamino)methyl-2-furanyl]methyl]thio]ethanamine in 10 ml of methanol is added, whereupon the mixture is stirred at room temperature until no further methoxy compound remains. It is necessary to add an additional 1.0 g of amine to complete the reaction. Afteer evaporation of solvent, the residue is chromatographed on silica gel using $CHCl_3$/methanol=25:1 as an eluant. Appropriate fractions are isolated and the solvent is removed in vacuo to give an oily product, which is then dissolved in 250 ml of ether and treated with methanol-HCl until no further precipitates form. The partially sticky solid is collected by filtration, washed with ether and small amounts of methanol, and then treated with acetone to give 5.37 g of a colorless solid. TLC (silica gel: $CHCl_3/CH_3OH=9.1$) Rf=0.54.

Because NMR indicates 2 molecules of HCl are incorporated, to prepare the final product the dichloride salt is dissolved in methanol, and the solution is adjusted to pH 6 using 1N-sodium methoxide. After evaporation of the solvent in vacuo, the residue is extracted with CHCl₃ and the CHCl₃ extracts evaporated in vacuo to dryness to yield the monochloride salt, m.p. 172°–174° C.

4-[2-(5-methyl-4-imidazolylmethylthio)-ethylamino]-4-oxo-1H,3H-pyrazolo[1,5-a]-1,3,5-triazine 4-[2-(5-methyl-4-imidazolylmethylthio)-ethylamino]-4-oxo-1H,3H-pyrazolo[1,5-a]-1,3,5-triazine is prepared from 2-methylthio-4-oxo-3H-pyrazolo[1,5-a]-1,3,5-triazine according to conventional methods.

8-bromo-4-2[-[[[5-(dimethylamino)methyl-2-furanyl]-methyl]thio]ethylamino-2-methylthio-pyrazolo[1,5-a]-1,3,5-triazine 8-bromo-4-2[-[[[5-(dimethylamino)methyl-2-furanyl]-methyl]thio]ethylamino-2-methylthio-pyrazolo[1,5-a]-1,3,5-triazine is prepared from 8-bromo-4-chloro-2-methylthiopyrazolo[1,5-a]-1,3,5-triazine and 2-[[[5-(dimethyl-amino)methyl-2-furanyl]methyl]thio]-ethanamine according to conventional methods.

Use

When administered to mammals alone or together with a pharmaceutically acceptable carrier substance (e.g. orally, topically, intravenously, parenterally, nasally, or by suppository), the compounds of the invention can prevent peptic, duodenal, and gastric ulcers. The compounds can also be used to treat reflex esophagitis, acute erosive gastritis, and pancreatic insufficiency.

The compounds of the invention can inhibit ulcers induced by non-steroidal anti-inflammatory drugs, e.g., aspirin and indomethacin, without inhibiting their anti-inflammatory and analgesic activity. Thus, the compounds can be particularly useful in treating or preventing gastric ulcers in patients, e.g., arthritics, who consume non-steroidal anti-inflammatory drugs. The anti-inflammatory action of the compounds can even reduce the dosage required of non-steroidal anti-inflammatory drugs. The compounds of the invention can also act as anti-depressants.

The compounds can be administered to a mammal in a dosage of 2 to 10 mg/kg/day, preferably 4 to 8 mg/kg/day.

Other embodiments are within the following claims.
We claim:

1. A compound having anti-ulcer activity and having the formula

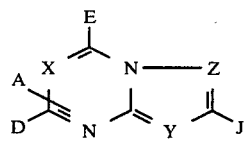

wherein D is H, SH, OH, R⁴S where R⁴ is a lower alkyl group containing between 1 and 7 carbon atoms, inclusive, or NH₂; E is OH or NH₂; J is H or phenyl; X is N; Y is, CH or CT, wherein T is a halogen; Z is N; A is

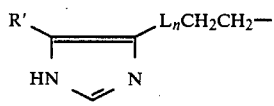

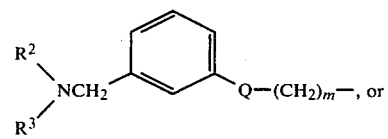

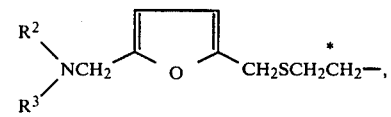

and replaces a hydrogen of, D or E; R¹ is H or CH₃; L is CH₂S; Q is O or CH₂S; n is 0 or 1; 2 m 4; each R² and R³, independently, is H, lower alkyl containing between 1 and 7 carbon atoms, inclusive, cycloalkyl containing between 3 and 6 carbon atoms, inclusive, benzyl, or phenethyl; or R² and R³, together with the nitrogen atom to which they are attached, form a morpholino, piperidino, or N-alkyl piperazino ring;
or a pharmaceutically acceptable salt thereof.

2. The compound of claim 1, wherein X is N; Z is N; J is H or phenyl; Y is CH or CT; and each R² and R³, independently, is H or a lower alkyl.

3. The compound of claim 1, wherein A is

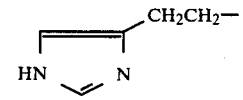

and is attached to D;
D is NH; E is OH, J is H; X is N; Y is CH; and Z is N;
said compound having the name 2-(4-imidazolyl-ethlamino)-4-oxo-1H,3H-pyrazolo[1,5-a]-1,3,5-triazine;
or a pharmaceutically acceptable salt thereof.

4. The compound of claim 1, wherein A is

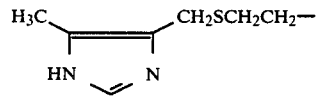

and is attached to E;
D is SCH₃; E is NH; J is H; X is N; Y is CH; and Z is N;
said compound having the name 4-(2-(5-methyl-4-imidazolylmethylthio)-ethylamino)-2-methylthiopyrazolo[1,5-a]-1,3,5-triazine;
or a pharmaceutically acceptable salt thereof.

5. The compound of claim 1, wherein A is

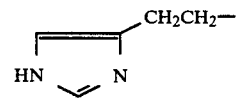

and is attached to E;
D is CH₃S; E is NH; J is H; X is N; Y is CH; and Z is N;

said compound having the name 4-(4-imidazolyl-ethylamino)-2-methylthiopyrazolo[1,5-a]-1,3,5-triazine;
or a pharmaceutically acceptable salt thereof.

6. The compound of claim 1, wherein
A is

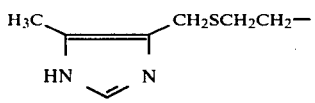

and is attached to E;
D is SCH$_3$; E is NH; J is H; X is N; Y is C—Br; and Z is N;
said compound having the name 8-bromo-4-(2-(5-methyl-4-imidazolylmethylthio)-ethylamino)-2-methylthiopyrazolo[1,5-a]-1,3,5-triazine;
or a pharmaceutically acceptable salt thereof.

7. The compound of claim 1, wherein
A is

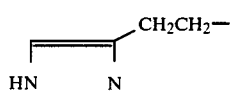

and is attached to E;
D is CH$_2$S; E is NH; J is H; X is N; Y is C—Br; and Z is N;
said compound having the name 8-bromo-4-(4-imidazolylethylamino)-2-methylthiopyrazolo[1,5-a]-1,3,5-triazine;
or a pharmaceutically acceptable salt thereof.

8. The compound of claim 1, wherein
A is

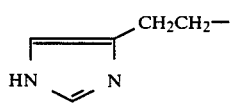

and is attached to E;
D is CH$_3$S; E is NH; J is Phenyl; X is N; Y is CH; and Z is N;
said compound having the name 4-[4-imidazolylethylamino]-2-methylthio-7-phenylpyrazolo[1,5-a]-1,3,5-triazine;
or a pharmaceutically acceptable salt thereof.

9. The compound of claim 1, wherein
A is

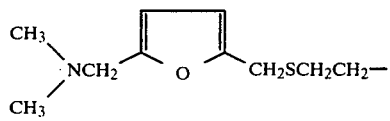

and is attached to E;
D is CH$_3$S; E is NH; J is Phenyl; X is N; Y is CH; and Z is N;
said compound having the name 4-2[-[[[5-(dimethylamino)methyl-2-furanyl]methyl]thio]ethylamino-2-methylthio-7-phenylpyrazolo[1,5-a]-1,3,5-triazine;
or a pharmaceutically acceptable salt thereof.

10. The compound of claim 1, wherein
A is

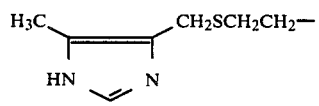

and is attached to D;
D is NH, E is OH; J is H; X is N; Y is CH; and Z is N;
said compound having the name 4-[2-(5-methyl-4-imidazolylmethylthio)-ethylamino]-4-oxo-1H,3H-pyrazolo[1,5-a]-1,3,5-triazine;
or a pharmaceutically acceptable salt thereof.

11. The compound of claim 1, wherein
A is

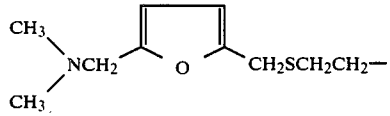

and is attached to E;
D is CH$_3$S; E is NH; J is H; X is N; Y is C—Br; and Z is N;
said compound having the name 8-bromo-4-2[-[[[5-(dimethylamino)methyl-2-furanyl]methyl]thio]ethylamino-2-methylthio-pyrazolo[1,5-a]-1,3,5-triazine;
or a pharmaceutically acceptable salt thereof.

12. A therapeutic composition for preventing or treating ulcers comprising a therapeutically effective amount of the compound of claim 1 together with a pharmaceutically acceptable carrier substance.

13. The therapeutic composition of claim 12 wherein said composition is in the form of a pill, tablet, capsule, or liquid for oral administration to a human patient in need of said compound.

14. A method of treating or preventing ulcers in a mammal comprising administering to said mammal an effective of the compound of claim 1.

* * * * *